United States Patent
Darrow et al.

(10) Patent No.: US 6,628,387 B2
(45) Date of Patent: Sep. 30, 2003

(54) INTERROGATION CRADLE AND INSERTABLE CONTAINMENT FIXTURE FOR DETECTING BIREFRINGENT MICROCRYSTALS IN BILE

(75) Inventors: Chris Darrow, Pleasanton, CA (US); Tino Seger, Berlin (DE)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/815,082

(22) Filed: Mar. 21, 2001

(65) Prior Publication Data

US 2002/0135765 A1 Sep. 26, 2002

Related U.S. Application Data (60) Provisional application No. 60/246,294, filed on Nov. 6, 2000.

(51) Int. Cl.⁷ ................................. G01J 4/00
(52) U.S. Cl. ............... 356/364; 356/336; 356/338; 356/436; 356/440
(58) Field of Search .................. 356/364, 365, 356/441, 243.2, 336, 338, 436, 440; 250/225; 137/142, 147, 148, 151; 604/208, 218, 232

(56) References Cited

U.S. PATENT DOCUMENTS

| | | | | |
|---|---|---|---|---|
| 3,695,763 A | * | 10/1972 | Shiuh | 356/441 |
| 3,856,408 A | * | 12/1974 | Hill et al. | 250/225 |
| 3,902,805 A | * | 9/1975 | Redner | 356/365 |
| 4,180,067 A | * | 12/1979 | Derlien | 604/143 |
| 4,266,874 A | * | 5/1981 | Janin et al. | 356/335 |
| 4,660,152 A | * | 4/1987 | Downing et al. | 356/442 |
| 4,912,059 A | * | 3/1990 | Newman et al. | 356/364 |
| 5,305,777 A | * | 4/1994 | Nakamura et al. | 137/102 |
| 5,620,309 A | * | 4/1997 | Todden et al. | 137/148 |
| 6,097,488 A | * | 8/2000 | Grek et al. | 356/364 |
| 6,157,448 A | * | 12/2000 | Kowa et al. | 356/365 |

FOREIGN PATENT DOCUMENTS

JP 63148147 A * 6/1988

* cited by examiner

*Primary Examiner*—Diane I. Lee
*Assistant Examiner*—Ahshik Kim
(74) *Attorney, Agent, or Firm*—James S. Tak; Alan H. Thompson (57) ABSTRACT

A transparent flow channel fluidly communicates a fluid source and a collection reservoir. An interrogating light beam passes through a first polarizer having a first plane of polarization. The flow channel is orthogonal to the light beam. The light beam passes through a fluid sample as it flows through the flow channel, and is then filtered through a second polarizer having a second plane of polarization rotated 90° from the first plane of polarization. An electronic photo-detector is aligned with the light beam, and signals the presence of birefringent microcrystals in the fluid sample by generating voltage pulses.

A disposable containment fixture includes the flow channel and the collection reservoir. The fixture is adapted for removable insertion into an interrogation cradle that includes optical and data processing components. The cradle rigidly positions the centerline of the flow channel orthogonal to the light beam.

41 Claims, 4 Drawing Sheets

INTERROGATION CRADLE AND INSERTABLE CONTAINMENT FIXTURE FOR DETECTING BIREFRINGENT MICROCRYSTALS IN BILE

This application claims priority from Provisional Patent Application Ser. No. 60/246,294, entitled "An Apparatus for Detecting Birefringent Mircrocrystals in Bile," filed Nov. 6, 2000, and incorporated herein by reference.

The United States Government has rights in this invention pursuant to Contract No. W-7405-ENG-48 between the United States Department of Energy and the University of California for the operation of Lawrence Livermore National Laboratory.

BACKGROUND OF THE INVENTION

Acute pancreatitis is a condition that affects over 200,000 persons annually in the United States. It is characterized by inflammation of the pancreas and severe abdominal pain. In extreme cases the illness can lead to renal and respiratory failure and even death. About 20% of all acute pancreatitis patients are considered idiopathic, that is, there is no known cause for the condition. Up to 75% of the idiopathic pancreatitis cases are associated with the presence of microcalculi, also known as microlithiasis, in the common bile duct. These are small stones believed to cause pancreatitis by transiently blocking the pancreatic duct that empties into the duodenum at the sphincter of Oddi.

To diagnose microlithiasis, patients typically undergo endoscopic retrograde cholangiopancreatography ("ERCP") by a gastroenterologist. In this procedure, the patient is sedated, and an endoscope is introduced orally and maneuvered through the stomach to the duodenum at the exit point of the common bile duct. A catheter is introduced into the bile duct through a working channel of the endoscope, and a sample of bile is aspirated from the patient. The patient is then discharged from the hospital and the bile sample is subsequently analyzed by laboratory personnel using a polarization microscope.

The presence of microlithiasis in the bile sample usually requires the pancreatitis patient to undergo further interventional treatment. The preferred treatment is usually a sphincterotomy, an endoscopic procedure in which a cut is made in the sphincter of Oddi to disrupt the sphincter and allow continual drainage of the bile duct. A sphincterotomy in cases of pancreatitis associated with microlithiasis has been shown to reduce the incidence of recurrent pancreatitis from 73% in the absence of a sphincterotomy, to 10% when the procedure has been performed. A sphincterotomy is preferable to the more invasive, involved and costly cholecystectomy, i. e., the surgical excision of the gall bladder.

A disadvantage of the above-described delayed analysis procedure is that the sphincterotomy must be accomplished through a second ERCP after the test result indicating the presence of microlithiasis becomes available. This additional procedure increases the cost of treating the condition and, for a second time, subjects the patient to the inherent risks associated with undergoing ERCP. If the gastroenterologist had knowledge of the presence of microlithiasis at the time of the first ERCP when a bile sample was collected, a sphincterotomy could be performed during the initial ERCP. A device that could make a rapid, intra-operative determination of the presence of microlithiasis could significantly reduce the medical expense when a sphincterotomy is called for.

The protocol for laboratory evaluation of bile for cholesterol microlithiasis varies among medical institutions, although a widely accepted standard is polarized-light microscopy. An example of the foregoing protocol for bile analysis is provided in Cynthia W. Ko, John H. Sekijima, M.D., and Sum P. Lee, M.D., Ph.D., "Billiary Sludge," *Annals of Internal Medicine*, Vol. 130 (1999), pp. 301–311. Bile is aspirated endoscopically from the patient after the administration of cholecystokinie ("CCK"). The CCK stimulates contraction of the gall bladder and relaxation of the sphincter of Oddi, thereby causing bile to flow out of the gall bladder, through the bile duct, and into the duodenum, where 2 to 5 milliliters of duodenal fluid, including bile, is collected. The sample is placed in a centrifuge tube and spun at 3000 g for 15 minutes.

Several microliters of sediment, suspended in a drop of distilled water, are transferred to a glass slide and examined by polarizing microscopy. When examined in this manner, cholesterol monohydrate crystals appear as bright, rhomboid-shaped plates or clumps of plates against a dark background. Ko et al. regard a positive test as finding more than two crystals of any type in a 100×magnified field or more than four crystals per sample.

The accuracy of the test results been called into question due to a lack of consensus in the medical community regarding the proper temperature at which the bile sample should be maintained prior to microscopic analysis. Some experts contend that cooling to this temperature inhibits bacterial growth during the unavoidable interval between drawing the sample and conducting the assay, while others maintain that cooling artificially induces the formation of precipitates that were not present in the sample in vivo. The accuracy of the test results thus depends whether the sample was cooled, and whether cooling ensures accuracy or is actually inimical to it.

In view of the foregoing, it can be seen that a need exists to provide a device that allows attending medical personnel to test for the presence of microlithiasis in bile during ERCP. More particularly, there is a need for a device that provides for relatively immediate microcrystal detection in bile extracted from a living organism. Such a device would allow the assay to be performed under known, controlled, and near life-like conditions during a period when further interventional treatment, i.e., sphincterotomy, could be immediately administered. Performing the assay immediately after the bile sample is withdrawn from the patient would moot the controversy over whether the bile sample should be cooled to inhibit bacterial growth, or whether such cooling in fact compromises the accuracy of the assay by inducing microcrystal precipitation in the sample.

Furthermore, having the results of an assay immediately available to the attending physician during ERCP would allow the physician, if warranted by the assay results, to immediately proceed with the administration of further interventional treatment. Since the diagnosis and treatment could be performed during the same ERCP, the patient would avoid the risks and discomfort associated with a second ERCP.

As may be seen from the foregoing, there presently exists a need in the art to rapidly detect crystalline materials in a fluid sample, e.g., bile, withdrawn from a patient undergoing ERCP, and thereby overcome the shortcomings, disadvantages and limitations of the prior art. The present invention fulfills this need in the art.

SUMMARY OF THE INVENTION

Briefly, the present invention is an apparatus for rapidly detecting crystalline materials such as cholesterol microcrystals in a fluid sample, e.g., a bile sample, withdrawn from a patient undergoing ERCP. The fluid sample flows through a transparent flow channel and into a collection reservoir. An interrogating light beam is polarized by an optical polarizer into a well-defined first plane of polarization. The transparent flow channel is situated orthogonal to the polarized interrogating light beam. The polarized light beam passes through the fluid sample as the fluid flows through the flow channel. The light beam is then directed to a second polarizer that passes only light having a plane of polarization that has undergone some degree of rotation relative to the first plane of polarization.

The birefringence of crystalline materials, such as microcrystalline cholesterol of times contained in the bile of patients suffering from pancreatitis, rotates the plane of polarization of the polarized light beam as it passes through the fluid sample. The presence of such microcrystals thus causes a portion of the interrogating beam to pass through the second polarizer and impinge an electronic photo-detector located in the path of the beam. The electronic photo-detector signals the detection of birefringent microcrystals by generating voltage pulses.

The device rapidly displays the quantitative results of the assay. It can be further configured to bar-code scan a patient's medical record number; find, retrieve and print out the designated medical record; and enter the record together with the results of the microcrystal detection test directly into a hospital's patient database via a built-in network interface.

A disposable fixture comprised of the flow channel and collection reservoir is adapted for removable insertion into an interrogation cradle. The fixture also includes some of the optics. The cradle includes the remainder of the optics and the electronic photo-detector. Attachment of the fixture to the cradle fixes the position of the flow channel relative to the interrogating beam, the optics, and the electronic photo-detector. In particular, the cradle keeps the flow channel centerline orthogonal to the interrogation beam. In addition, the foregoing configuration keeps the sample fluid contained within the fixture during its interrogation, and provides for its convenient disposal along with the detached fixture after the test is completed.

These and other features, aspects and advantages of the present invention will become better understood with reference to the following drawings, description and claims.

DETAILED DESCRIPTION OF THE INVENTION

The apparatus of the invention is usually used in conjunction with an ERCP of a sedated patient. It allows attending medical personnel to detect the presence or ascertain the absence of birefringent microcrystals, e.g., cholesterol, in a patient's bile within a brief period after the removal of the bile sample so that, if called for, the attending gastroenterologist can proceed with a sphincterotomy in conjunction with the ERCP while the patient is still sedated. For example, the assay results would almost always be known in less than five minutes, often in less than two minutes, and many times in less than one minute.

Figure 1:
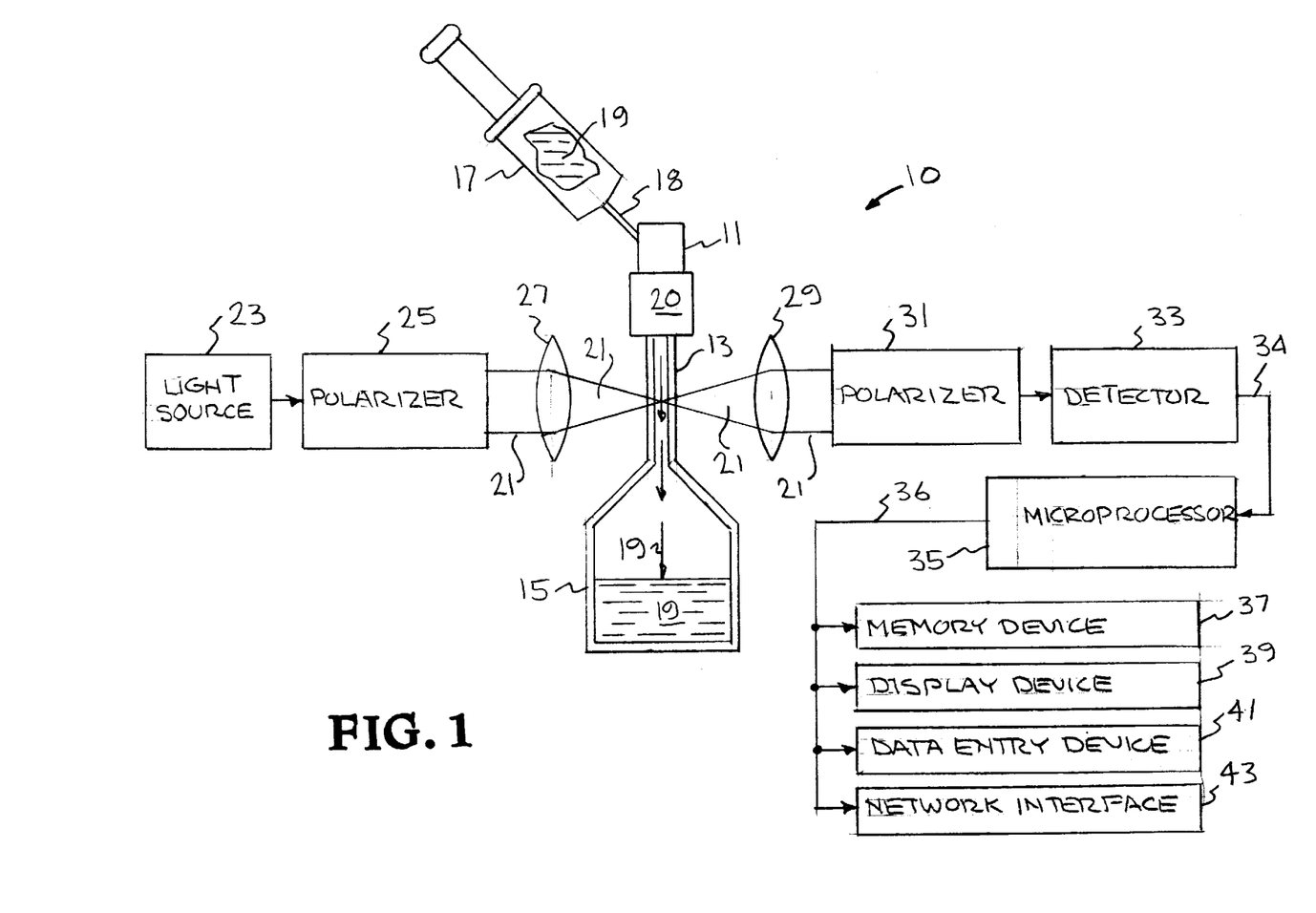
FIG. 1 is a schematic drawing depicting an embodiment of the microcrystal detection device of the present invention, and particularly describing the optics and data processing elements.

Turning to the drawings, FIG. 1 schematically illustrates test apparatus 10, an embodiment of the invention including intake fitting 11, tubular flow channel 13, and collection reservoir 15. Flow channel 13 is transparent. A suitable fluid dispensing means, for example, syringe 17, is used to collect fluid 19, e. g., bile, from a patient and inject fluid 19 into and through intake fitting 11. Intake fitting 11 is a "Luer" type fitting that provides a sealed, fluid-tight connection between syringe 17 and flow channel 13 when tip 18 of syringe 17 is inserted therein, and incorporates one-way check valve 20 that allows fluid 19 to enter flow channel 13, but prevents it from escaping. Syringe 17 forces fluid 19 through flow channel 13 and into collection reservoir 15. The direction of flow of fluid 19 is thus parallel to the axial centerline of flow channel 13.

Interrogating light beam 21 is a beam of light emitted by light source 23, and is preferably directed orthogonal to the direction of flow of fluid 19. Beam 21 is passed through polarizer 25, creating a light beam having a well-defined polarization orientation. Beam 21, after being polarized, passes through focusing lens 27 that focuses beam 21 into a relatively small focal region lying within the inner lateral cross-section defined by the inner walls of flow channel 13. After emerging from flow channel 13, beam 21 then passes through collector lens 29, which collects and relays it to polarizer 31. Polarizer 31 passes only light having a plane of polarization that is rotated 90° relative to the plane of polarization of the light passing through polarizer 25. Thus, polarizer 31 blocks light that has retained the original polarization that was selected by polarizer 25. Any portion of beam 21 passing through polarizer 31 impinges electronic photo-detector 33.

In the absence of birefringent microcrystals in fluid 19, virtually no light passes through the polarizer 31 because polarizer 31 rejects the polarized light in beam 21 that passed through polarizer 25 and that passed without further rotation through fluid 19 in flow channel 13. However, when a birefringent crystalline material, e.g., microlithiasis, passes through the focal region of beam 21, a small fraction of the incident light is intercepted by and passes through the crystalline material, emerging from flow channel 13 with a resultant polarization that is rotated from its original plane of polarization. Only the portion of light in beam 21 having a plane of polarization rotated 90° from its plane of polarization on entering flow channel 13 can pass through polarizer 31 and impinge electronic photo-detector 33.

Thus, passage of the crystalline material through beam 21 causes electronic photo-detector 33 to generate electronic signals 34. Each of signals 34 is comprised of a voltage pulse having a duration corresponding to the period that the moving crystalline material lies within the focal region of beam 21. Signals 34 are input into microprocessor 35, which is appropriately programmed to accept or reject each of signals 34 on the basis of its amplitude or duration, or its amplitude and duration.

After all of fluid 19 has flowed through flow channel 13, the final microcrystal count, as represented by processed signal data 36, is input into and recorded by memory device 37, and presented in numerical or graphic form on display device 39. Thus, test apparatus 10 provides an estimate of the total number of microcrystals of a detectable size present per unit volume of fluid 19. The accuracy of the device can be periodically checked by performing an assay on a test sample composed of a calibration solution containing a known concentration of insoluble birefringent microcrystals.

Processed signal data 36 may also be combined with data entered through the data entry device 41 and routed over a network using a network interface 43. Data entry device 41 allows patient-specific data, e.g., bar-coded patient identification and date information, to be attached to the assay data file. Network interface 43 transmits the assay results to a database, e.g., a hospital patient database.

In addition to functions associated with collection, processing and routing of data, microprocessor 35 could also be programmed to control the assay procedure. For example, an electrical connection between an appropriately programmed microprocessor 35 and a fluid pump connected to syringe 17 could automatically command the pumping fluid 19 through flow channel 13 at the appropriate time in the assay cycle.

The f-number of focusing lens 27 (equal to a lens' focal length divided by its diameter) is selected to ensure that its focal region covers most of the inner lateral cross section of flow channel 13. If the focal region of focusing lens 27 is too small, a significant part of flow channel 13 would lie outside of the focal region, and thus a substantial portion of fluid 19 would not be examined. This would adversely affect the accuracy of the assay. The f-number of collector lens 29 is selected to ensure that beam 21 exiting the focal region is relayed to polarizer 31 and electronic photo-detector 33 without unnecessary losses.

If the microcrystal count is sufficiently high, the number of undetected microcrystals, e. g., microcrystals passing outside of the focal region, can be statistically estimated within a reasonable certainty. When an even more accurate determination of the degree of microlithiasis is desired, the flow column of fluid 19 can be hydrodynamically focused in flow channel 13 to ensure complete overlap of the focal region of beam 21 and the flow column.

Various light sources can be employed. Solid-state devices such as light emitting diodes ("LEDs") and visible-wavelength diode lasers provide superior reliability, cost savings, and simplicity, although LEDs typically require a more elaborate focusing lens 27 to achieve a satisfactory focal region within flow channel 13. Diode lasers can be efficiently focused and therefore provide effective signal levels. Additional alternatives include exotic lasers as well as incandescent, electroluminescent and gas-discharge sources.

Figure 2:
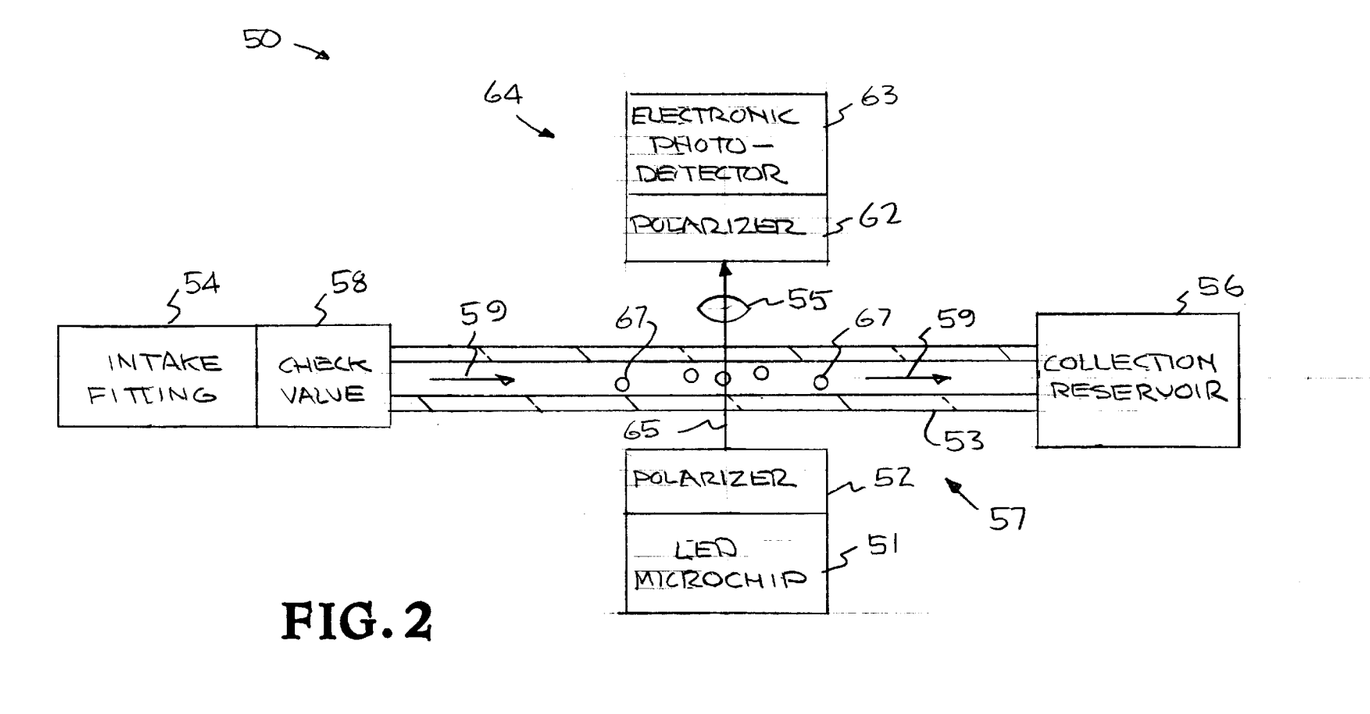
FIG. 2 is a schematic drawing illustrating another embodiment of the microcrystal detection device of the present invention that integrates an LED chip, a flow channel and some of the optics into a disposable fixture that is removably inserted into an interrogation cradle.

As schematically illustrated in FIG. 2, microcrystal detection apparatus 50 comprises an alternative embodiment that integrates LED microchip 51, thin-film polarizer 52, transparent flow channel 53, intake fitting 54, optic collector lens 55, and collection reservoir 56; into containment fixture 57. More particularly, LED microchip 51 lies adjacent and is rigidly affixed to thin-film polarizer 52. Flow channel 53 fluidly communicates intake fitting 54 with collection reservoir 56. Intake fitting 54 is a "Luer" type fitting that incorporates one-way check valve 58 allowing fluid to enter flow channel 53, but preventing its escape.

The inner diameter of flow channel 53 typically ranges from approximately 100 to 500 microns. Suitable fluid dispensing means, for example, a syringe, is used to collect fluid 59, e. g., bile, from a patient and inject it into flow channel 53 via intake fitting 54. The fluid dispensing means applies a pressure to fluid 59 that is greater than the pressure in flow channel 53 and collection reservoir 56, to force fluid 59 to flow through flow channel 53 and into collection reservoir 56.

Polarizer 62 and electronic photo-detector 63 comprise interrogation cradle 64. When fluid 59 is to be examined, containment fixture 57 is removably attached to interrogation cradle 64 by mechanical means (not shown) well known to those skilled in the relevant art.

When containment fixture 57 is attached to interrogation cradle 64, thin-film polarizer 52 is placed in stationary contact with flow channel 53. LED microchip 51 emits interrogating light beam 65 in the direction of thin-film polarizer 52 and flow channel 53. More particularly, beam 65 orthogonally intersects the axial centerline of flow channel 53.

Beam 65 is polarized by thin-film polarizer 52, and subsequently passes through fluid 59 flowing axially through flow channel 53. Beam 65 is then collected by optic collector lens 55 and directed through polarizer 62, which is oriented to pass only light waves having a plane of polarization orthogonal to the plane of polarization of light waves passing through thin-film polarizer 52. The light waves passing through polarizer 62 impinge detector 63. Birefringent microcrystals 67 suspended in fluid 59 and passing through beam 65, rotate the plane of polarization of some fraction of the light composing beam 65, and thus cause detector 63 to generate voltage pulses and signal their presence.

Microcrystal detection apparatus 50 does not require a focusing lens because LED microchip 51 lies in proximity to flow channel 53. This design simplifies the optical configuration of the apparatus and reduces the cost of apparatus 50 relative to that of related microcrystal detection apparatus 10. Moreover, since the foregoing configuration fixes the position of flow channel 53 with respect to the source and collector optics, i.e., thin-film polarizer 52 and collector lens 55, it virtually eliminates misalignment between the aforementioned optical components. Furthermore, since alignment error between LED microchip 51 and detector 63 is cumulative, this configuration increases the alignment tolerance between flow channel 53 and detector 63, thus increasing the overall reliability of microcrystal detection apparatus 50.

In addition, fluid 59 is sealed and contained within containment fixture 57 both during and after its interrogation. In particular, after the completion of the interrogation, containment fixture 57 is detached from interrogation cradle 64 and disposed of together with fluid 59 contained therein. The foregoing feature of microcrystal detection apparatus 50 substantially reduces the probability that either medical personnel or other patients will physically contact fluid 59.

Figure 3A:
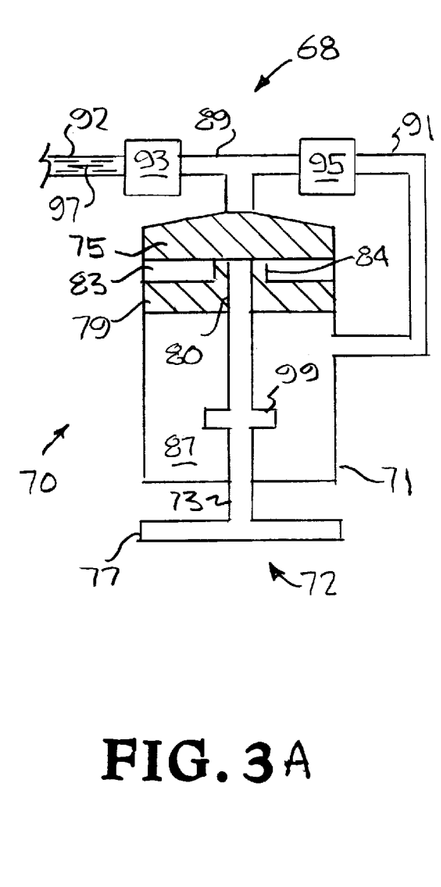
FIGS. 3A, 3B, and 3C schematically illustrates a fixture of the present invention for containing a fluid sample having two pistons to force the fluid sample through a flow channel, wherein it can be examined by an interrogating light beam.

As an alternative to integrating several of the optical components into a disposable fluid-containment fixture, the present invention can also be configured to isolate all of the optical components as part of an interrogation cradle separate from the disposable fluid-containment fixture. As schematically illustrated in FIG. 3A, microcrystal detection apparatus 68 comprises such an embodiment of the present invention, and is particularly directed to avoiding contamination of medical personnel and other patients by the fluid being examined.

Microcrystal detection apparatus 68 is comprised of fluid containment fixture 70 and an interrogation cradle (not shown). Fluid containment fixture 70 includes hollow cylindrical housing 71 and plunger 72 contained therein. Plunger 72 includes shaft 73, primary piston 75 and handle 77, with primary piston 75 and handle 77 being attached to opposite ends of shaft 73 such that primary piston 75 remains within housing 71 and handle 77 remains outside of housing 71 during the operational cycle of fluid containment fixture 70. The circumference of primary piston 75 is in slideable contact with the inner diameter of housing 71 by flexible sealing means which prevent fluid from passing between the two elements even when they are moving with respect to one another.

Secondary piston 79 is also located within housing 71, and has hole 80 in its center through which shaft 73 is slidably disposed. The circumference of secondary piston 79 is in slidable contact with the inner diameter of housing 71. The slidable contact between shaft 73 and hole 80, and between the circumference of secondary piston 79 and the inner diameter of housing 71, is obtained using flexible sealing means that prevents fluid from passing between the two adjacent elements even when they are moving with respect to one another.

Secondary piston 79 is floating in the sense that its motion is opposed only by friction where it slidably contacts the inner diameter of housing 71 and the circumference of plunger shaft 73. Secondary piston 79 is therefore able to move independently of shaft 73 and primary piston 75.

Variable intermediate volume 83 is formed in between primary piston 75 and secondary piston 79, with its minimum value being maintained by spacer 84. Spacer 84 is integral to secondary piston 79, although spacer 84 could alternatively be fixedly attached to primary piston 75 or free floating on shaft 73. There are two other variable volumes located within housing 71: intake volume 85, which is formed in between the head of primary piston 75 and housing 71, and air volume 87, which is formed in between secondary piston 79 and housing 71. Air volume 87 is not sealed where housing 71 circumscribes shaft 73. Air volume 87 thus fluidly communicates with and remains at the local atmospheric pressure.

T-section 89 and flow channel 91 fluidly communicate inlet 92 with housing 71. T-section 89 includes one-way check valves 93 and 95. Fluid 97 is drawn into fluid containment fixture 70 through inlet 92 by means of the axial intake stroke of plunger 72 in combination with the action of check valves 93 and 95, as will be described in conjunction with the following example detailing the use of apparatus 68 to assay bile drawn from a patient during an ERCP.

Figure 3B:
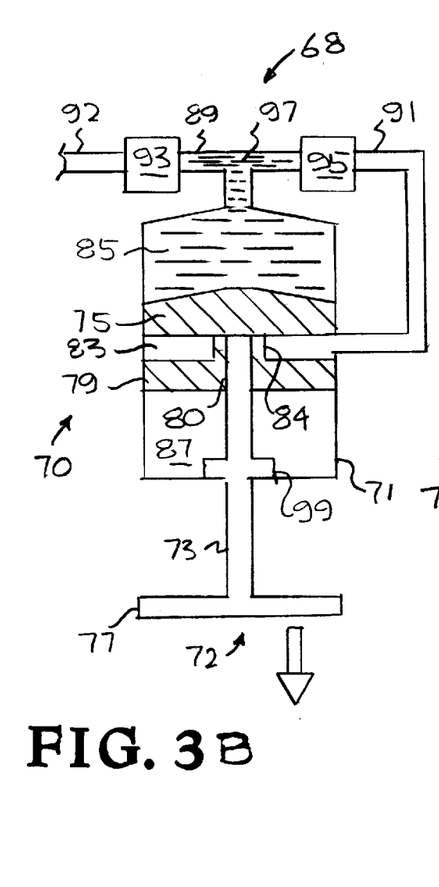

Inlet 92 is used to directly aspirate fluid 97 comprised of bile, from a catheter placed in a working channel of an endoscope during an ERCP. FIG. 3A shows plunger 72 and secondary piston 79 in their initial positions. They are held in place by friction between each of them and the internal diameter of housing 71. As shown in FIG. 3B, when plunger 72 is pulled out of housing 71 by force being applied to handle 77, fluid 97 is drawn through check valve 93 and T-section 89, and into intake volume 85 formed inside of housing 71. The travel distance of plunger 72 is limited by stop 99, which is fixedly attached to shaft 73. This is the intake stroke of plunger 72.

As primary piston 75 presses downward against spacer 84 during the intake stroke, secondary piston 79 is forced downward. When stop 99 abuts housing 71, the intake stroke is completed and intermediate volume 83, empty at this time, is aligned with and communicates with flow channel 91. During the intake stroke, fluid 97 is prevented from entering flow channel 91 by the pressure in T-section 89 being slightly lower than that in flow channel 91 due to the increasing volume of intake volume 85.

After the completion of the intake stroke, fluid containment fixture 70 is attached to the interrogation cradle so that the axial axis of flow channel 91 lies orthogonal to the path of interrogating light beam 101. The interrogation cradle includes a light source that generates light beam 101, first and second polarizers, focusing and collector lenses, and a photo-electric detector, which jointly operate to examine fluid 97 for the presence of microcrystals as explained in conjunction with the description of test apparatus 10.

Figure 3C:
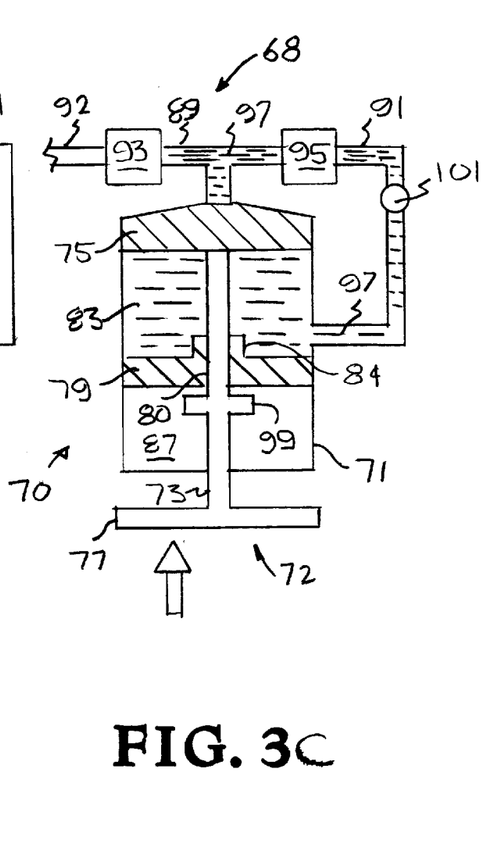

As illustrated in FIG. 3C, plunger 72 is then pushed back into housing 71, comprising the compression stroke. The upward movement of primary piston 75 compresses intake volume 85, forcing fluid 97 through T-section 89 and check valve 95; into flow channel 91 and through beam 101; and finally into expanded intermediate volume 83.

After the assay has been completed and the results have been displayed by the interrogation cradle, fluid containment fixture 70 is detached from the interrogation cradle and disposed of. An unused fluid containment fixture 70 is subsequently used in the foregoing manner for the next patient. At all times during the operation of microcrystal detection apparatus 68, fluid 97 is contained within disposable fluid containment fixture 70, thereby eliminating the risk of it physically contacting either medical personnel or the interrogation cradle.

Figure 4A:
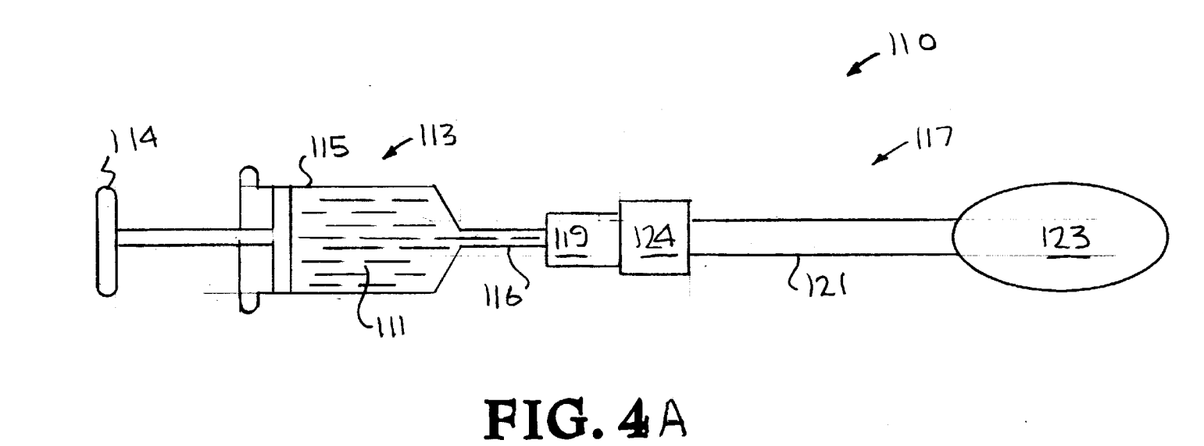
FIGS. 4A and 4B schematically illustrates another fixture of the present invention that uses an inflatable collection reservoir to contain the fluid sample.

Microcrystal detection apparatus 110, as schematically illustrated in FIG. 4A, comprises another embodiment present invention. The following example, wherein apparatus 110 is used to assay bile 111 drawn from a medical patient, is used only as an aid to facilitate understanding of the embodiment, and is not intended to preclude or otherwise limit its beneficial application in other disciplines.

Bile 111 is first aspirated from a catheter placed in a working channel of an ERCP endoscope using custom-sized, but otherwise conventional syringe 113. Syringe 113 includes plunger 114, housing 115, and tip 116. Apparatus 110 is comprised of fluid containment fixture 117 and an interrogation cradle (not shown). Fluid containment fixture 117 includes fitting 119, flow channel 121, and collection reservoir 123.

More particularly, fitting 119 is a "Luer" type fitting that provides a sealed, fluid-tight connection between tip 116 and flow channel 121 when tip 116 is inserted therein, and incorporates one-way check valve 124 that allows fluid to enter flow channel 121, but prevents it from escaping. Collection reservoir 123 is inflatable and collapsible. To that end, collection reservoir 123 is constructed of a flexible but robust polymeric material that allows it to expand to contain bile 111 as bile 111 is forced to flow into reservoir 123 by the fluid pressure generated by syringe 113.

To begin the assay process, tip 116 of syringe 113 containing bile 111 is inserted into fitting 119. The assembly composed of syringe 113 and fixture 117 is then inserted into the interrogation cradle of apparatus 110. The interrogation cradle is configured to precisely align flow channel 121 orthogonal to interrogating light beam 125 when fixture 117 is inserted into the interrogation cradle. The interrogation cradle includes a light source for generating interrogating light beam 125, first and second polarizers, focusing and collector lenses, and a photo-electric detector, which jointly operate to examine bile 111 for the presence of microcrystals as explained in conjunction with the description of test apparatus 10.

Figure 4B:
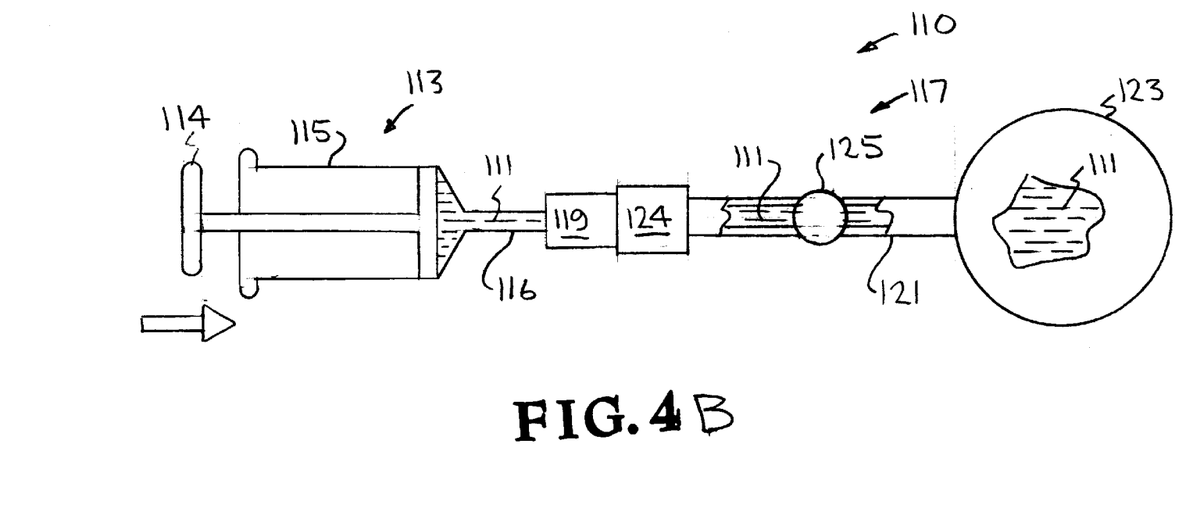

As shown in FIG. 4B, plunger 114 is then forced into housing 115 of syringe 113. This forces bile 111 out of syringe 113, through fitting 119 and check valve 124, and into flow channel 121. While flowing through flow channel 121, bile 111 passes through and is interrogated by beam 125. Bile 111 then flows into and inflates collection reservoir 123.

After the assay has been completed and the results have been displayed by the interrogation cradle, fixture 117 is detached from the interrogation cradle and disposed of. Syringe 113 preferably remains inserted in fitting 119, and is disposed of along with fixture 117. An unused fixture 117 is subsequently used in the foregoing manner for the next patient. At all times during and after the operation of apparatus 110, bile 111 remains sealably contained within the disposable assembly comprised of syringe 113 and fixture 117, thereby eliminating the risk of it contaminating either medical personnel or the interrogation cradle.

In another embodiment that is not illustrated, collapsible collection reservoir 123 is replaced by a rigid cylindrical reservoir including a free-floating, captive piston. Inflow of bile 111 displaces the piston and fills the cylindrical reservoir. This embodiment lends itself to economical manufacture and, in using a rigid collection reservoir, provides for secure containment of bile 111 as a precaution should fixture 117 be dropped or otherwise mishandled.

It should be understood, of course, that the foregoing descriptions relate to preferred embodiments of the invention and that modifications may be made without departing from the spirit and scope of the invention as set forth in the following claims.

What is claimed is:

1. A microcrystal detection apparatus comprising:
    a transparent flow channel;
    a first polarizing means for polarizing light into a first plane of polarization;
    a second polarizing means for polarizing light into a second plane of polarization;
    said second plane of polarization being rotated relative to said first plane of polarization;
    a detection means for detecting a component of an associated interrogating light beam passing through said first polarizing means, said flow channel and said second polarizing means; and
    a cradle adapted for attaching said flow channel thereto, for aligning said light beam, said flow channel, and said detection means, whereby
    a birefringent crystalline material in an associated fluid flowing through said flow channel causes said light beam to include said light beam component, thereby allowing said light beam component to impinge said detection means and signal the presence of said birefringent crystalline material.

2. The microcrystal detection apparatus recited in claim 1 wherein said cradle includes said detection means.

3. The microcrystal detection apparatus recited in claim 2 wherein said second plane of rotation is rotated 90° relative to said first plane of rotation.

4. The microcrystal detection apparatus recited in claim 3 wherein said cradle further includes said second polarizing means.

5. The microcrystal detection apparatus recited in claim 4 further comprising: a fixture; and
    said fixture including said flow channel and said first polarizing means.

6. The microcrystal detection apparatus recited in claim 5 wherein said fixture further includes a light source for emitting said light beam.

7. The microcrystal detection apparatus recited in claim 6 wherein said fixture further includes a collector lens for directing said light beam toward said second polarizing means.

8. The microcrystal detection apparatus recited in claim 7 wherein said flow channel lies orthogonal to said light beam when said fixture is attached to said cradle.

9. The microcrystal detection apparatus recited in claim 8 wherein said fixture includes a collection reservoir fluidly communicating with said flow channel, for storing said fluid after said fluid has flowed through said flow channel.

10. The microcrystal detection apparatus recited in claim 9 wherein said collection reservoir has a variable fluid capacity.

11. The microcrystal detection apparatus recited in claim 9 wherein said collection reservoir is inflatable.

12. The microcrystal detection apparatus recited in claim 10 wherein said fixture further includes:
    a fitting for communicating said flow channel with a source of said fluid; and
    said fitting includes a check valve that allows fluid flow only into said flow channel.

13. The microcrystal detection apparatus recited in claim 12 wherein said detection means emits a signal to indicate impingement of said light beam component.

14. The microcrystal detection apparatus recited in claim 13 wherein said signal is an electrical impulse.

15. The microcrystal detection apparatus recited in claim 14 further comprising:
    display means for displaying said signal;
    storage means for storing said signal; and
    interface means for transmitting said signal over a computer network.

16. The microcrystal detection apparatus recited in claim 15 further comprising means for automatically controlling a flow of said fluid from said fluid source into said flow channel.

17. The microcrystal detection apparatus recited in claim 4 wherein said cradle further includes said first polarizing means.

18. The microcrystal detection apparatus recited in claim 17 wherein said cradle further includes a collector lens for directing said light beam toward said second polarizing means.

19. The microcrystal detection apparatus recited in claim 18 wherein said flow channel lies orthogonal to said light beam when said flow channel is attached to said cradle.

20. The microcrystal detection apparatus recited in claim 19 further comprising:
    a focusing lens for focusing said light beam into a focal region;
    said flow channel having inner walls and an inner lateral cross section defined by said inner walls; and
    at least a portion of said inner lateral cross section lying within said focal region.

21. The microcrystal detection apparatus recited in claim 20 wherein said second plane of polarization is rotated 90° relative to said first plane of polarization.

22. The microcrystal detection apparatus recited in claim 21 wherein said collector lens lies in between said focal region and said second polarizing means.

23. The microcrystal detection apparatus recited in claim 22 wherein said cradle further includes a light source for emitting said light beam.

24. The microcrystal detection apparatus recited in claim 23 further comprising a collection reservoir fluidly communicating with said flow channel, for storing said fluid after said fluid has flowed through said flow channel.

25. The microcrystal detection apparatus recited in claim 24 wherein said collection reservoir has a variable fluid capacity.

26. The microcrystal detection apparatus recited in claim 24 wherein said collection reservoir is inflatable.

27. The microcrystal detection apparatus recited in claim 26 wherein said detection means emits a signal to indicate impingement of said light beam component.

28. The microcrystal detection apparatus recited in claim 27 wherein said signal is an electrical impulse.

29. The microcrystal detection apparatus recited in claim 28 further comprising:
   display means for displaying said signal;
   storage means for storing said signal; and
   interface means for transmitting said signal over a computer network.

30. The microcrystal detection apparatus recited in claim 29 further comprising means for automatically controlling a flow of said fluid from said fluid source into said flow channel.

31. The microcrystal detection apparatus recited in claim 29 wherein said flow channel further includes:
   a fitting for communicating said flow channel with a source of said fluid; and
   said fitting includes a check valve that allows fluid flow only into said flow channel.

32. The microcrystal detection apparatus recited in claim 23 further comprising:
   a housing having a primary piston and a secondary piston slidably disposed therein;
   an intake reservoir within said housing, formed between said housing and said primary piston; and
   a collection reservoir within said housing, formed between said primary piston and said secondary piston; wherein
      said flow channel fluidly communicates said intake reservoir and said collection reservoir.

33. The microcrystal detection apparatus recited in claim 32 further comprising:
   a T-section for fluidly communicating said intake reservoir with said flow channel;
   a first one-way check valve located in between said T-section and said flow channel, whereby
      said fluid can flow only from said T-section into said flow channel;
   an inlet for fluidly communicating said T-section with a source of said fluid; and
   a second one-way check valve located in between said T-section and said inlet, whereby
      said fluid can flow only from said inlet into said T-section.

34. The microcrystal detection apparatus recited in claim 33 wherein said primary piston is for drawing said fluid into said intake reservoir, and for forcing said fluid into said flow channel and into said collection reservoir.

35. An apparatus for interrogating and storing a fluid comprising:
   a fixture for containing said fluid;
   said fixture including a transparent flow channel for fluidly communicating said fluid within said fixture;
   a light source for emitting an interrogating light beam for examining said fluid as said fluid flows through said flow channel; and
   a cradle adapted for attaching said fixture thereto, for positioning said flow channel to intersect said light beam,
   whereby a birefringent crystalline material in an associated fluid flowing through said flow channel may be interrogated by the light beam to determine the presence of said birefringent crystalline material.

36. The fluid interrogation and storage apparatus recited in claim 35 wherein:
   said fixture includes a collection reservoir for storing said fluid after said fluid has been examined by said interrogation beam; and
   said collection reservoir communicates with said flow channel.

37. The microcrystal detection apparatus recited in claim 36 wherein said cradle is for positioning said flow channel orthogonal to said light beam.

38. The fluid interrogation and storage apparatus recited in claim 37 wherein said fixture includes means for forcing said fluid to flow through said flow channel and into said collection reservoir.

39. An apparatus for interrogating and storing a fluid comprising:
   a fixture for containing said fluid, said fixture including a transparent flow channel for fluidly communicating said fluid within said fixture, a housing, a primary piston and a secondary piston slidably disposed within said housing, an intake reservoir within said housing, formed between said housing and said primary piston, a collection reservoir within said housing, formed between said primary piston and said secondary piston, and said flow channel fluidly communicating said intake reservoir with said collection reservoir;
   a light source for emitting an interrogating light beam for examining said fluid as said fluid flows through said flow channel; and
   a cradle adapted for attaching said fixture thereto, for positioning said flow channel to intersect said light beam.

40. The fluid interrogation and storage detection apparatus recited in claim 39 wherein said fixture further comprises:
   a T-section for fluidly communicating said intake reservoir with said flow channel;
   a first one-way check valve located in between said T-section and said flow channel, whereby
      said fluid can flow only from said T-section into said flow channel;
   an inlet for fluidly communicating said T-section with a source of said fluid; and
   a second one-way check valve located in between said T-section and said inlet, whereby
      said fluid can flow only from said inlet into said T-section.

41. The fluid interrogation and storage apparatus recited in claim 40 wherein said primary piston is for drawing said fluid into said intake reservoir, and for forcing said fluid through said flow channel and into said collection reservoir.

* * * * *